US00PP36257P2

(12) United States Plant Patent
Van Swieten

(10) Patent No.: US PP36,257 P2
(45) Date of Patent: Nov. 19, 2024

(54) ***PHALAENOPSIS* ORCHID PLANT NAMED 'PHA578420'**

(50) Latin Name: ***Phalaenopsis* hybrid**
Varietal Denomination: PHA578420

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/831,074

(22) Filed: Jun. 6, 2024

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHA578420', particularly characterized by having numerous attractive, small, orange striped and netted flowers with reddish-purple lips, gentle scent, ligulate lateral lobes, and is propagated by meristem tissue culture, is disclosed.

3 Drawing Sheets

Genus and species: *Phalaenopsis* hybrid.
Variety denomination: 'PHA578420'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA578420'.

The new *Phalaenopsis* plant is a product of a planned breeding program conducted by the inventor in Bleiswijk, the Netherlands. The objective of this breeding program was to create a new *Phalaenopsis* plant with numerous attractive, small, orange striped and netted flowers with reddish-purple lips suitable for potted plant production.

The new *Phalaenopsis* plant 'PHA578420' is a result of cross-pollination made by the inventor in December 2016 in Bleiswijk, the Netherlands, of the proprietary female, or seed parent, *Phalaenopsis* hybrid '12-054117-0003' (unpatented) with the proprietary male, or pollen parent, *Phalaenopsis* hybrid 'PHALHUCAR' (U.S. Plant Pat. No. 32,955).

The new *Phalaenopsis* was selected by the inventor as a single plant within the progeny of the stated cross-pollination in a controlled greenhouse in Bleiswijk, the Netherlands, in October 2019. Asexual reproduction of the new *Phalaenopsis* plant by meristem tissue culture since 2020 in Bleiswijk, the Netherlands, has demonstrated that the new variety reproduces true to type with all the characteristics, as herein described, firmly fixed and retained through successive generations.

Community Plant Variety Rights for this variety have been applied for in the European Union on Aug. 17, 2023 (Application no. 2023/1719), by Applicant who obtained the subject matter disclosed directly from the inventor.

'PHA578420' has not been made publicly available or sold anywhere in the world prior to the effective filing date of this application with the exception of sales or disclosures made one year or less before the effective filing date of this claimed invention by Applicant who obtained 'PHA578420' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA578420' as a new and distinct variety of *Phalaenopsis* plant:

1. Small, orange striped and netted flowers with reddish-purple lips;
2. Flowers have a very gentle scent;
3. Lateral lobe shape is ligulate;
4. Bump and ridge on apical lobe is large;
5. Whiskers on the lips are absent; and
6. Peduncle: anthocyanin coloration is weak.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 42-week-old plants in April 2024. Colors in the photographs may differ from the color values cited in the detailed botanical description, which accurately describe the actual colors of the new variety.

DESCRIPTION OF THE NEW VARIETY

Figure 1:
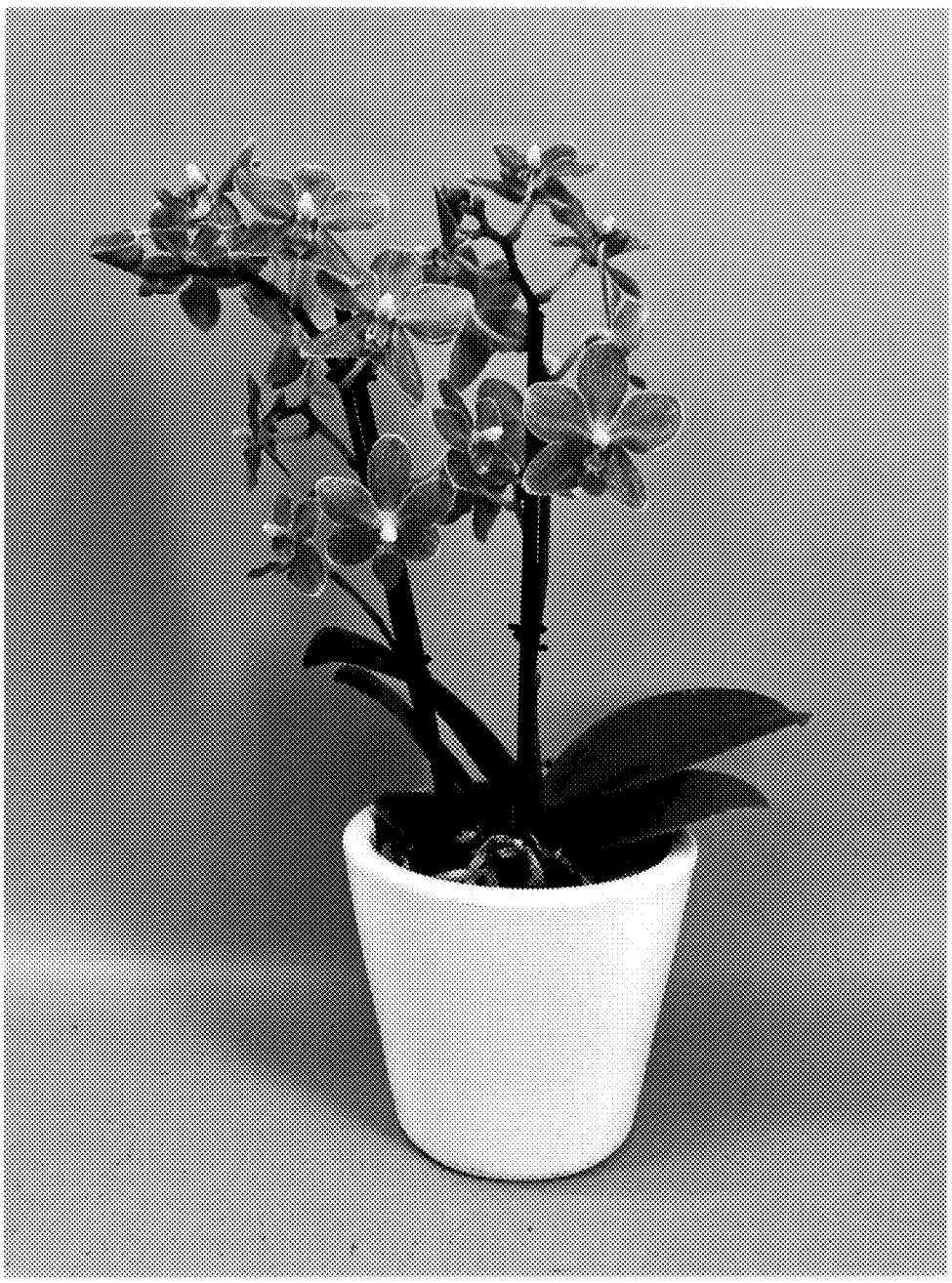
FIG. 1 shows the overall plant habit, including blooms, buds, and foliage of 'PHA578420'.
Figure 2:
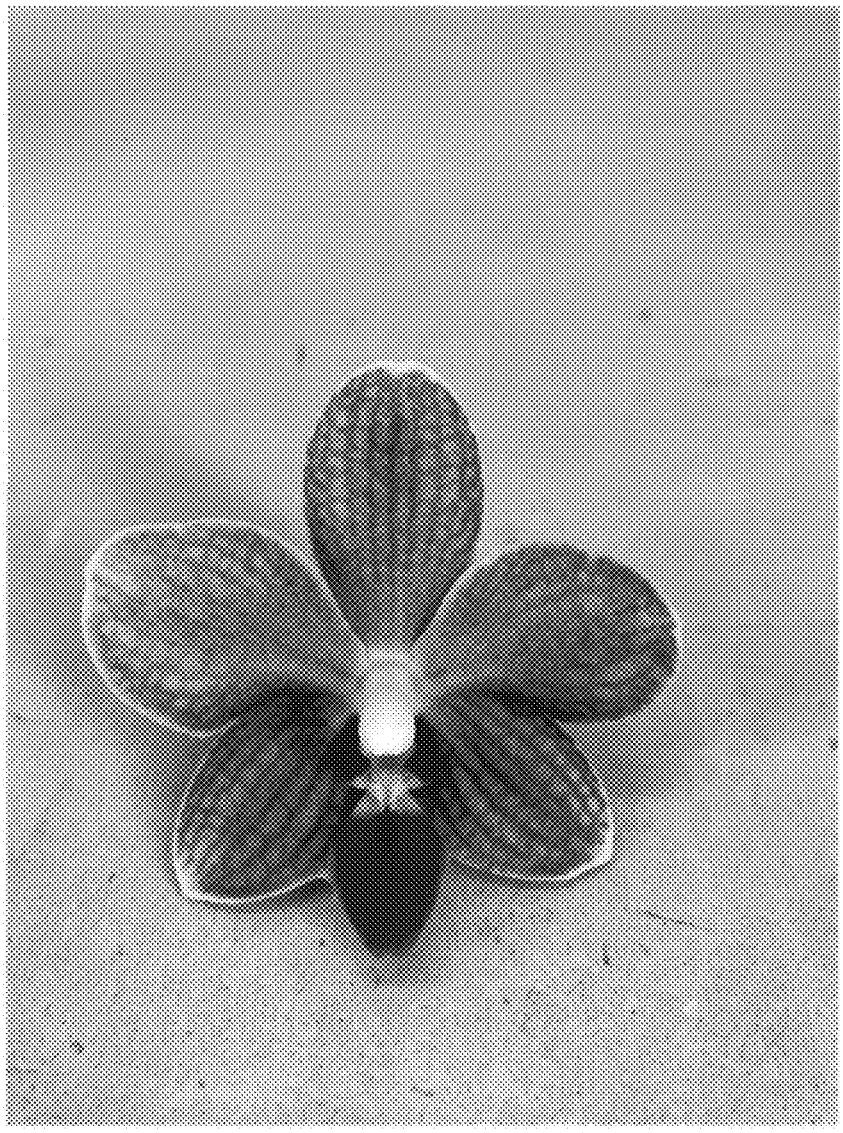
FIG. 2 shows a close-up of a flower of 'PHA578420'.
Figure 3:
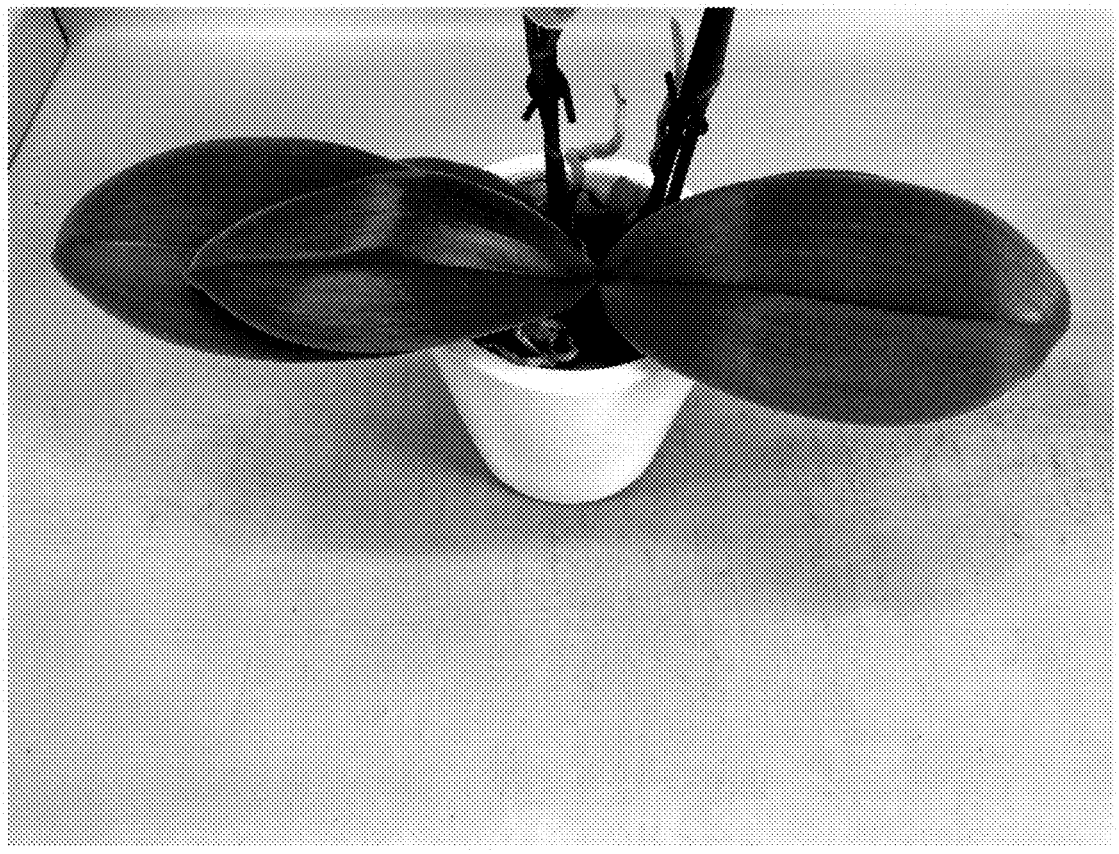
FIG. 3 shows an overhead, close-up view of the leaves of 'PHA578420'.

The following detailed description sets forth the distinctive characteristics of 'PHA578420'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2024 on flowering plants which were planted in 9-centimeter (diameter) pots. After in vitro propagation, the plants were grown in nursery trays for 18-20 weeks, followed by transplantation to 9-centimeter (diameter) pots and grown in a greenhouse between 27° C. to 29° C. for 25 weeks, continued by a cooling period of 6 weeks between 18° C. to 20° C. and 11 weeks in a greenhouse of 21° C. Flowering occurs after 42 weeks in 9-centimeter pots.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHA578420'.

Parentage:
- *Female parent*.—*Phalaenopsis* cultivar '12-054117-0003' (unpatented).
- *Male parent*.—*Phalaenopsis* cultivar 'PHALHUCAR' (U.S. Plant Pat. No. 32,955).

Propagation:
- *Type*.—Meristem tissue culture.

Roots:
- *Root description*.—Greyed-green colored roots (a color in between RHS 190B and RHS 190C) with branching lateral roots having light yellow-green colored root tips (RHS 145A).

Plant:
- *Crop time to flowering*.—Following asexual propagation (in vitro), the rooted cuttings grow for 18-20 weeks. After transplantation into 9-cm pots, the plants are finished after 40 to 42 weeks.
- *Growth habit of the peduncle*.—Upright to slightly pendent with panicle inflorescence.
- *Height* (*from soil level to top of inflorescence*).—Approximately 25.0 cm to 30.0 cm.
- *Width* (*measured from leaf tips*).—About 29.0 cm to 31.0 cm.
- *Vigor*.—Strong.

Leaves:
- *Mature leaves*.—Quantity per plant: 7 to 8 leaves are produced before flowering. Length (fully expanded): 14.0 cm to 16.0 cm. Width: 6.5 cm to 7.5 cm. Position of the broadest part of the leaf: At the middle. Shape: Oblong. Base shape: Moderately elongated. Apex: Obtuse asymmetric. Leaf blade angle with the petiole (measured from the horizontal position): Between 10 degrees and 25 degrees. Leaf margin: Entire. Color: Upper surface: RHS 147A. Lower surface: RHS 147B. Texture (both upper and lower surfaces): Smooth. Thickness: 1.0 mm to 2.0 mm. Variegation: Absent. Venation: Pattern: Parallel. Color of the midvein: Upper surface: RHS 147A. Lower surface: RHS 146A.

Peduncle:
- *Quantity per plant*.—2.
- *Number of flowers per peduncle*.—12 to 17.
- *Length*.—25.0 cm to 30.0 cm.
- *Diameter*.—3.0 mm to 4.0 mm.
- *Strength*.—Strong.
- *Aspect*.—Upright to slightly pendent.
- *Texture*.—Smooth.
- *Color*.—Green (RHS 146B) with a gentle touch of brown (RHS N199B).
- *Internode length*.—2.0 cm to 2.5 cm.

Inflorescence description:
- *Appearance*.—Upright to slightly pendent, panicle inflorescence with bilaterally symmetrical flowers that open in succession beginning with the lowermost flower.
- *Number of inflorescences*.—2.
- *Inflorescence size*.—Height (from base to tip): 140.0 mm to 190.0 mm.
- *Flowering time*.—First flowers can be expected 7 to 8 months after planting in a 9-cm (diameter) pot.
- *Flower*.—Height: 50.0 mm to 55.0 mm. Diameter: 45.0 mm to 50.0 mm. Depth of lip: 15.0 mm to 17.0 mm.
- *Flower shape*.—Straight.
- *Flower longevity*.—On the plant: 13 to 15 weeks.
- *Fragrance*.—Present, but very light.
- *Flower bud*.—Average size: Medium. Length: 16.0 mm to 18.0 mm. Width: 12.0 mm to 14.0 mm. Shape: Egg shaped. Color: Yellow-green (RHS 144C) with a gentle touch of red (RHS 183D) at the base; yellow-green (RHS 144B) toward the tip.
- *Petals*.—Arrangement: Open/free. Shape: Moderately elongated. Apex: Rounded asymmetric. Margin: Weakly undulated. Length (from base to tip): 21.0 mm to 23.0 mm. Width: 18.0 mm to 20.0 mm. Position of the broadest part of the petal: Toward the apex. Color (when fully opened): Upper surface: Basic color: Greenish-yellow (RHS 3A). Over color: Reddish-orange (RHS 175D). Lower surface: Basic color: Yellow (RHS 153D). Over color: Reddish-orange (RHS 176C). Number of spots, dots, and stripes on the petals (upper surface): Medium stripes. Color of spots, dots, and stripes on the petals (upper surface): RHS 59B. Density of netting of the petals (upper surface): High. Color of the netting (upper surface): RHS 59B.
- *Dorsal sepal*.—Shape: Moderately elongated. Apex: Emarginated symmetric. Margin: Entire. Length (from base to tip): 29.0 mm to 31.0 mm. Width: 15.0 mm to 17.0 mm. Position of the broadest part of the dorsal sepals: Toward the tip. Color (when fully opened): Upper surface: Basic color: Greenish-yellow (RHS 3A). Over color: Purplish-red (RHS 186A) at the base; reddish-orange (RHS 175D). Lower surface: Basic color: Yellow (RHS 153D). Over color: A gentle touch of reddish-orange (RHS 175D) toward margins; greenish-yellow (RHS 151A) toward the tip. Number of spots, dots, and stripes on the dorsal sepals (upper surface): Few to medium stripes. Color of spots, dots, and stripes on the dorsal sepals (upper surface): RHS 59A. Density of netting of the dorsal sepals (upper surface): High. Color of the netting (upper surface): RHS 59A.

*Lateral sepals*.—Shape: Ovate. Apex: Obtuse asymmetric. Margin: Entire. Length (from base to tip): 24.0 mm to 26.0 mm. Width: 16.0 mm to 18.0 mm. Position of the broadest part of the lateral sepals: Toward the base. Color (when fully opened): Upper surface: Basic color: Greenish-yellow (RHS 3A). Over color: Reddish-orange (RHS 176C). Lower surface: Basic color: Greenish-yellow (RHS 153C). Over color: A touch of very light purple (RHS 76C) at the base; greenish-yellow midvein and tip (RHS 151A); gentle touch of orange (RHS 167C) toward margins on sides. Number of spots, dots, and stripes on the lateral sepals (upper surface): Few stripes. Color of spots, dots, and stripes on the lateral sepals (upper surface): RHS 59A. Density of netting of the lateral sepals (upper surface): High. Color of the netting (upper surface): RHS 59A.

*Labellum* (*lip*).—Whiskers: Absent. Pubescence on the lip: Absent.

*Lateral lobe*.—Shape: Type I (as described in the International Union for the Protection of New Varieties of Plants (UPOV) Test Guidelines for *Phalaenopsis*); ligulate. Margin: Entire. Length: 9.0 mm to 10.0 mm. Width: 3.0 mm to 4.0 mm. Color: Upper surface: White (RHS NN155C); gentle touch of yellow (RHS 9A) and dotted RHS 59B at the base; purplish-red RHS 59B toward the tip. Lower surface: White (RHS NN155C); purplish-red (a color in between RHS 59B and RHS 59C) toward tip. Number of spots and stripes on the lateral lobe: Medium to many of very small dots. Color of spots and stripes on the lateral lobe: RHS 59B. Density of netting of the lateral lobe: None. Color of the netting: None.

*Apical lobe*.—Shape: Elliptic. Margin: Entire. Length: 13.0 mm to 15.0 mm. Width: 8.0 mm to 10.0 mm. Color: Upper surface: Touch of white (RHS NN155D) at the base; red (RHS 46A); touch of greenish-yellow (RHS 153C) toward margin on sides; purplish-red (RHS 59C) at the middle toward the tip. Lower surface: Very light purple (a color in between RHS 76B and RHS 76C) at the middle from base toward the tip; touch of yellow (RHS 163C) and purplish-red (RHS 59C) toward margin. Number of spots and stripes on the apical lobe: None. Color of spots and stripes on the apical lobe: Not applicable. Density of netting of the apical lobe: None. Color of the netting: Not applicable. Bump and ridge: Present (large).

*Callus*.—Average size: Small. Height: 2.0 mm to 3.0 mm. Length: 2.0 mm to 3.0 mm. Width: 2.0 mm to 3.0 mm. Color: White (RHS NN155A) with very small purplish-red dots (RHS 59B) and yellow (RHS 13A) toward tips.

Reproductive organs:

*Column*.—Length: 8.0 mm to 10.0 mm. Diameter: 3.0 mm to 4.0 mm. Color: Very light purple (RHS 76C) at the base with white tips (RHS NN155C).

*Pollinia*.—Quantity: 2. Diameter: 0.8 mm to 0.9 mm. Color: Orange-yellow (RHS 23A).

*Ovary*.—Length: 7.0 mm to 9.0 mm. Diameter: 1.7 mm to 1.9 mm.

*Pedicel*.—Length: 27.0 mm to 29.0 mm. Diameter: 2.1 mm to 2.3 mm. Color: Light yellow-green (RHS 145B) at the base; lighter yellow-green (RHS 145C) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA578420' differs from the female parent plant '12-054117-0003' (unpatented) in that 'PHA578420' has a high density of netting, elliptic apical lobes, and medium curvature of lateral lobes, whereas '12-054117-0003' has a low density of netting, trullate to elliptic apical lobes, and weak curvature of lateral lobes.

'PHA578420' differs from the male parent plant 'PHALHUCAR' (U.S. Plant Pat. No. 32,955) in that 'PHA578420' has elliptic apical lobes, high density of netting with no spots on the petals, and narrower flowers, whereas 'PHALHUCAR' has rhombic apical lobes, no netting with very many spots on the petals, and wider flowers.

'PHA578420' is most similar to the commercial *Phalaenopsis* plants named 'PHALGASCIJ' (U.S. Plant Pat. No. 32,286) and 'PHALGURZON' (U.S. Plant Pat. No. 31,708). 'PHA578420' differs from the commercial variety 'PHALGASCIJ' in that 'PHA578420' has panicle inflorescences, narrower flowers with moderately elongated petals that are narrower, and no whiskers, whereas 'PHALGASCIJ' has raceme inflorescence, wider flowers with medium to moderately elongated petals that are much wider, and very short whiskers.

'PHA578420' differs from the commercial variety 'PHALGURZON' in that 'PHA578420' has narrower flowers with moderately elongated petals that are narrower than 'PHALGURZON', is absent of whiskers, and absent or weak anthocyanin coloration, whereas 'PHALGURZON' has wider flowers with medium petals that are wider than 'PHA578420', whiskers, and medium to strong anthocyanin coloration.

I claim:

1. A new and distinct variety of *Phalaenopsis* plant named 'PHA578420', substantially as described and illustrated herein.

* * * * *